United States Patent [19]

Louderback

[11] 4,324,685

[45] Apr. 13, 1982

[54] BLOOD SERUM REFERENCE STANDARD

[75] Inventor: Allan L. Louderback, Temple City, Calif.

[73] Assignee: Beckman Instruments, Inc., Fullerton, Calif.

[21] Appl. No.: 132,609

[22] Filed: Mar. 21, 1980

Related U.S. Application Data

[63] Continuation of Ser. No. 925,481, Jul. 17, 1978, abandoned.

[51] Int. Cl.³ .................... G01N 33/16; C09K 3/00
[52] U.S. Cl. .................... 252/408; 23/230 B; 424/2; 424/3; 435/4
[58] Field of Search .................... 252/408; 23/230 B; 424/2, 3; 435/4

[56] References Cited

U.S. PATENT DOCUMENTS

| | | | |
|---|---|---|---|
| 3,466,249 | 9/1969 | Anderson | 252/408 |
| 3,629,142 | 12/1971 | Marbach | 252/408 |
| 3,681,255 | 8/1972 | Wilfore | 252/408 |
| 3,876,375 | 4/1975 | Maurukas | 252/408 |
| 4,001,142 | 1/1977 | Turner | 252/408 |
| 4,007,008 | 2/1977 | Becker et al. | 252/408 |
| 4,141,856 | 2/1979 | Dorwart, Jr. et al. | 252/408 |

*Primary Examiner*—Teddy S. Gron
*Attorney, Agent, or Firm*—R. J. Steinmeyer; Robert S. Frieman

[57] ABSTRACT

An improved blood serum reference composition of the type comprising blood serum having constituents of known values, characterized in that said composition further comprises a water soluble amine chloride. The water soluble amine chloride is employed to adjust the negative electrolyte balance of said reference composition without interfering with presently employed blood serum clinical assay procedures or analytical equipment used therein.

5 Claims, No Drawings

BLOOD SERUM REFERENCE STANDARD

This is a continuation, of application Ser. No., 925,481, filed July 17, 1978, now abandoned.

BACKGROUND OF THE INVENTION

1. Field of the Invention

This invention relates to a stable blood serum reference composition capable of use as a blood serum reference control or a blood serum reference standard and to a method of preparation and use thereof.

2. Description of the Prior Art

There are several electrolytes in serum that must be examined in order to determine the health of a patient. These electrolytes are sodium and potassium (which possess a positive charge) and chloride and bicarbonate (which possess a negative charge).

Bicarbonate and carbon dioxide are interrelated by the following equation:

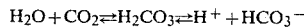

Therefore, clinical laboratories sometimes assay for carbon dioxide instead of bicarbonate.

Most control serums currently used in clinical laboratories contain all of these electrolytes for calibration purposes.

One prior art blood serum reference standard is described in U.S. Pat. No. 3,466,246 (hereinafter referred to as Anderson), said patent being incorporated herein in toto by reference. Anderson discloses a stable blood serum reference standard having a standard carbon dioxide content wherein a freeze-dried blood serum component of the reference standard is reconstituted with an aqueous ammonium bicarbonate component of the reference standard. The blood serum reference standard disclosed by Anderson is undesirable because of the myriad problems encountered due to the presence of the ammonium ion therein. For example, the ammonium ion contaminates solid state potassium and sodium electrodes as well as interferes with various clinical procedures such as the Berthlot reaction for urea nitrogen and the glutamic dehydrogenase reaction for urea nitrogen. In addition, excess ammonium ions also inhibit various enzymes, e.g., urease.

Another reference standard blood serum for the calibration of automatic blood serum analyzing apparatus is disclosed in U.S. Pat. No. 3,629,142 (hereinafter referred to as Marbach), said patent also being incorporated in toto by reference. The reference standard blood serum of Marbach contains trihydroxymethylamine (Tris) carbonate so as to permit it to be reconstituted just prior to use with distilled water so as to restore a predetermined carbon dioxide level in the reference serum. Although the reference standard blood serum of Marbach overcomes several of the problems inherent in Anderson's blood serum reference standard (see Marbach, column 2, lines 25–48), the amine group sticking off the Tris employed in Marbach's reference standard acts as a competitive inhibitor of urease and thereby also interferes in various clinical assays.

SUMMARY OF THE INVENTION

The instant invention encompasses an improved blood serum reference composition of the type comprising blood serum having constituents of known values, characterized in that said composition further comprises a water soluble amine chloride. The water soluble amine chloride neither interferes with currently employed clinical assay procedures nor with current analyzing apparatus employed to conduct said procedures.

The invention also encompasses the process for adjusting the total ion balance of a blood serum reference composition. This process comprises sequentially adding sodium bicarbonate to said composition to adjust its bicarbonate level to a desired amount; adding sodium chloride to said composition to adjust its sodium level to a desired amount; adding potassium chloride to the composition to adjust its total potassium level to a desired amount; and adding a water soluble amine chloride to the composition to adjust its total chloride level to a desired amount.

In addition to the above, the instant invention further encompasses a process and diluent for use therein for reconstituting a freeze-dried blood serum reference composition. The diluent comprises a water soluble amine chloride and a composition selected from a group consisting of sodium carbonate and sodium bicarbonate.

DESCRIPTION OF THE PREFERRED EMBODIMENTS

The improved blood serum reference composition of the instant invention is of the type which comprises blood serum having constituents of known values. The instant invention's blood serum reference composition is characterized in that it further comprises a water soluble amine chloride.

Virtually any water soluble amine chloride known to those skilled in the art can be employed in the blood serum reference composition of the instant invention. Because of the explosive nature of various amine chlorides, it is preferred to select the water soluble amine chloride from a group consisting of

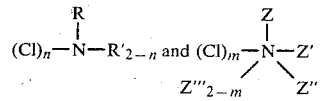

wherein R, R', Z, Z', Z'', and Z''' are independently selected from a group consisting of hydrogen, hydroxyl, and alcohol, ketone, carboxylic acid, ester, and ether groups containing from 1 to 5 carbon atoms and wherein n and m are independently integers from 1 to 2. It is further preferred that R, R', Z, Z', Z'', and Z''' are independently selected from the group consisting of hydrogen and saturated alcohol, saturated ketone, saturated carboxylic acid, saturated ester, and saturated ether groups containing 1 to 5, more preferably 1 to 2, carbon atoms.

Desirable water soluble amine chlorides include, but are not limited to, dimethylamine hydrochloride, diethylamine hydrochloride, tetramethylamine, hydrochloride, tetraethylamine hydrochloride, monomethylamine hydrochloride, monoethylamine hydrochloride, trimethylamine hydrochloride, and triethylamine hydrochloride.

Virtually any blood serum reference composition is improved when a water soluble amine chloride is employed therein to adjust the chloride balance of said composition. A preferred blood serum reference composition wherein said water soluble amine chloride can be employed is described in U.S. Pat. No. 3,876,375 (hereinafter referred to as Maurukas), said patent being incorporated herein in toto by reference. The biological reference control composition of Maurukas comprises in its nonbiological component from about 60 to about 80 weight percent water, from about 20 to about 40 weight percent of at least one alkylene polyol having from about 2 to about 5 carbon atoms, the remainder being chiefly at least one natural biological material selected from a group consisting of blood serum, enzymes, metabolites, electrolytes, and hormones. However, it is also possible, but not preferable, to employ in the instant invention a biological reference control composition which comprises in its nonbiological component from about 40 to about 85 weight percent water and from about 15 to about 60 weight percent of said polyol, the remainder being as stated above.

There are various techniques for preparing blood serum reference compositions. The serum prepared via these techniques contain sodium, potassium, chloride, and bicarbonate values below those normally found in blood serum reference compositions. Typically, these values might be of the order shown in Table I.

TABLE I

| Ingredient | Concentration, MEQ/L |
|---|---|
| Sodium (Na) | 50 |
| Potassium (K) | 1 |
| Chloride (Cl) | 15 |
| Bicarbonate ($HCO_3$) | 2 |

To be suitable for use as reference standard or as a reference control, the serum should have an electrolyte content as listed in Table II.

TABLE II

| Electrolyte | Concentration, MEQ/L |
|---|---|
| Na | 110–160 |
| K | 3.5–8.5 |
| Cl | 85–135 |
| $HCO_3$ | 20–40 |

To adjust the serum's electrolyte balance to a desired level within that shown in Table II, one should employ the following process:

(a) add sodium bicarbonate to the serum to adjust the serum's bicarbonate level to a desired amount and subtract from the amount of sodium desired, the amount of sodium added as sodium bicarbonate;

(b) add sodium chloride to the serum to adjust the serum's sodium level to a desired amount and subtract from the amount of chloride needed the amount of chloride added as sodium chloride;

(c) add potassium chloride to the serum to adjust the serum's total potassium level to a desired amount and subtract from the amount of chloride needed the amount of chloride added as potassium chloride; and (d) add a water soluble amine chloride to the serum to adjust its total chloride level to the desired amount.

It should be obvious to one skilled in the art that the above steps can be performed in various sequences, the only critical factor being the addition of the water soluble amine chloride.

If one wishes to employ a freeze-dried blood reference composition, the carbon dioxide will out gas during the lypholization procedure. Therefore, it is necessary to add to the freeze-dried blood serum reference composition a diluent comprising a water soluble amine chloride and a compound selected from a group consisting of sodium carbonate and sodium bicarbonate.

The improved blood serum reference compositions of the instant invention can be employed as blood serum reference standards or as blood serum reference controls, i.e., the compositions can be employed to calibrate an instrument or can be employed to periodically verify that the instrument is still operating within the tolerances desired.

Based upon the above disclosure, many other modifications and ramifications will naturally suggest themselves to those skilled in the art. These are also intended to be encompassed within the scope of the instant invention.

The embodiments of the invention in which an exclusive property or privilege is claimed are defined as follows:

1. An improved blood serum reference composition of the type comprising blood serum having constituents of known values, characterized in that said standard further comprises a water soluble amine chloride selected from a group consisting of dimethylamine hydrochloride, diethylamine hydrochloride, monomethylamine hydrochloride, monoethylamine hydrochloride, trimethylamine hydrochloride, and triethylamine hydrochloride.

2. An improved biological reference control composition for use in analysis of biologically similar unknowns, of the type comprising in its non-biological component from about 60 to about 80 weight percent water, from about 20 to about 40 weight percent of at least one alkylene polyol having from about 2 to 5 carbon atoms, the remainder being chiefly at least one natural biological material selected from a group consisting of blood serum, enzymes, metabolites, electrolytes, and hormones, characterized in that said composition further comprises a water soluble amine chloride selected from a group consisting of dimethylamine hydrochloride, monomethylamine hydrochloride, monoethylamine hydrochloride, trimethylamine hydrochloride, and triethylamine hydrochloride.

3. A process for adjusting the total ion balace of a blood serum reference composition comprising:
   (a) adding sodium bicarbonate to said composition to adjust its bicarbonate level to a desired amount;
   (b) adding sodium chloride to said composition to adjust its sodium level to a desired amount;
   (c) adding potassium chloride to said composition to adjust the total potassium level to a desired amount; and
   (d) adding a water soluble amine chloride selected from a group consisting of dimethylamine hydrochloride, diethylamine hydrochloride, monomethylamine hydrochloride, monoethylamine hydrochloride, trimethylamine hydrochloride, and triethylamine hydrochloride to said composition to adjust its total chloride level to a desired amount.

4. A process for reconstituting a freeze-dried blood serum reference composition comprising blood serum having constituents of known values comprising adding to said freeze-dried standard a diluent comprising a water soluble amine chloride selected from a group consisting of dimethylamine hydrochloride, diethylamine hydrochloride, monomethylamine hydrochloride, monoethylamine hydrochloride, trimethylamine hydrochloride, and triethylamine hydrochloride and a composition selected from a group consisting of sodium carbonate and sodium bicarbonate.

5. A diluent comprising a water soluble amine chloride selected from a group consisting of dimethylamine hydrochloride, diethylamine hydrochloride, monomethylamine hydrochloride, monoethylamine hydrochloride, trimethylamine hydrochloride, and triethylamine hydrochloride and a composition selected from a group consisting of sodium carbonate and sodium bicarbonate.

* * * * *